United States Patent [19]

Wilder et al.

[11] 4,377,166

[45] Mar. 22, 1983

[54] SURGICAL EVACUATOR

[76] Inventors: Joseph R. Wilder, 151 W. 86th St., New York, N.Y. 10024; Franklin G. Reick, 228 W. Place, Westwood, N.J. 07675; Frederick R. Picut, Rte. 22, Driveway 4, Mountainside, N.J. 07092

[21] Appl. No.: 238,177

[22] Filed: Mar. 27, 1972

Related U.S. Application Data

[63] Continuation-in-part of Ser. No. 57,288, Jul. 22, 1970.

[51] Int. Cl.³ .............................................. A61M 1/00
[52] U.S. Cl. ................................................... 128/278
[58] Field of Search ............................ 128/276–278, 128/297–300, 145.7, 281; 417/234, 395, 437, 470, 472, 474, 479, 544, 568

[56] References Cited

U.S. PATENT DOCUMENTS

| | | | |
|---|---|---|---|
| 11,300 | 7/1854 | Clemens | 417/479 |
| 37,677 | 2/1863 | Colvin | 128/281 |
| 3,111,125 | 11/1963 | Schulte | 128/350 V |
| 3,376,868 | 4/1968 | Mondiadis | 128/278 |
| 3,425,409 | 2/1969 | Isaacson et al. | 128/145.7 |
| 3,461,808 | 8/1969 | Nelson et al. | 417/479 |
| 3,572,340 | 3/1971 | Lloyd et al. | 128/278 |
| 4,141,361 | 2/1979 | Snyder | 128/278 |

Primary Examiner—John D. Yasko
Attorney, Agent, or Firm—Michael Ebert

[57] ABSTRACT

A manually-operated surgical evacuator for draining fluids from the human body. The evacuator is constituted by a cup of rigid material covered by an elastic membrane to define a sump chamber, the cup being provided with an inlet fixture and an exhaust fixture communicating with the chamber. The inlet fixture is coupled by a suitable tube to the wound to be drained, and the exhaust fixture is provided with a removable plug or other means to open and shut the exhaust. Attached to the membrane is a rigid disc functioning as an actuator, such that when the plug is removed and the disc pressed into the cup, the membrane is stretched inwardly and acts to displace the atmosphere through the open exhaust fixture. After the exhaust fixture is shut and the disc released, the membrane proceeds to return to its original form, thereby creating a negative pressure which acts to draw fluid from the wound through the tube and into the sump chamber.

1 Claim, 4 Drawing Figures

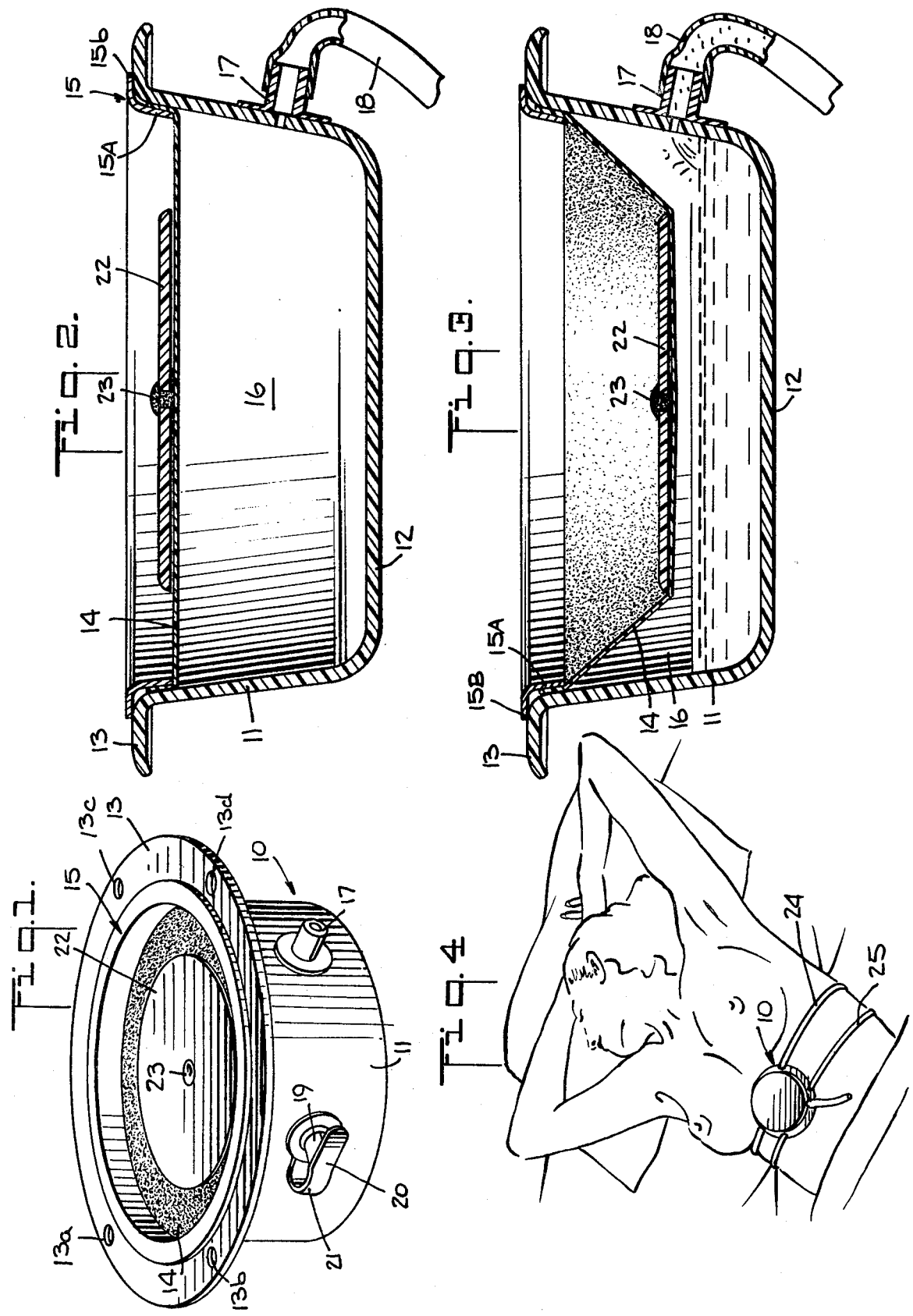

SURGICAL EVACUATOR

This application is a continuation-in-part of our co-pending application Ser. No. 57,288, filed July 22, 1970.

BACKGROUND OF THE INVENTION

This invention relates generally to surgical evacuators for withdrawing fluid from the human body, and more particularly to a manually-operated evacuator of exceptionally simple and efficient design.

In post-operative surgical procedures, drains are used whenever an abnormal collection of fluid is encountered, be it contaminated or infected material, blood, bile or lymph, exudate or transudate. Ordinary wounds are normally drained for a post-operative period running as long as forty-eight hours. Effective drainage is of medical importance, for swelling and tension are minimized thereby, post-operative pain is reduced, and wound edges are maintained flat and quiescent.

In order to do away with costly electrical and mechanical drainage pumps, it is known to use a manually-operated evacuator, such as the type disclosed in U.S. Pat. No. 3,115,138. This evacuator is constituted by a collapsible, fluid-tight, flexible container having rigid top and bottom plates therein which are engaged by helical springs acting to separate the plates. When the plates are pressed together to collapse the container, the springs therebetween are compressed to reduce the volume of the container, thereby exhausting the atmosphere from the container through an open discharge outlet. When the outlet is closed and the plates are thereafter released, the springs act to return the collapsed container to its original shape. The resultant partial vacuum produces a suction force which acts to draw fluid from an operative wound through a drain tube coupled to the container.

While such manually-operated evacuators are less costly than electrical and mechanical pumps, they nevertheless have a relatively complex structure and are fairly difficult and expensive to manufacture. Moreover, since evacuators of this type are discarded after use on a patient, the cost of the evacuator may become a major hospital expense, for hundreds of such evacuators are used in a typical city hospital in the course of a year.

Also, in a conventional, manually-operated evacuator, the drain tube inlet and the discharge outlet are mounted on the top wall of the collapsible container which includes the rigid top plate. The reason for this is that the flexible side wall of the container is collapsed when the container is compressed. It is not feasible, therefore, to place the inlet and outlet in the side wall, for the tube and plug associated therewith may be dislodged when the container is compressed.

On the other hand, with the inlet and outlet mounted on the top wall of the container, one must be careful, when pressing the wall down to evacuate the atmosphere, not to dislodge the associated tube and plug, as this makes it inconvenient to apply adequate manual pressure to the container to fully exhaust the atmosphere therein. The amount of negative pressure depends, of course, on the extent to which the container is collapsed, and should only a partial collapse be effected, the resultant negative pressure may be inadequate to carry out effective drainage.

SUMMARY OF THE INVENTION

In view of the foregoing, it is the main object of this invention to provide an exceptionally simple and efficient manually-operated surgical evacuator which obviates the need for electrical and mechanical pumps to drain operative wounds.

More specifically, it is an object of this invention to provide an evacuator of the above type, which is disposable and may be produced at very low cost, the evacuator being free of springs and other relatively costly elements.

Also an object of the invention is to provide an evacuator having inlet and exhaust fixtures which are mounted on a rigid side wall, the fixtures being unaffected by the manual operation of the evacuator, so that the elements coupled thereto are undisturbed by this operation, thereby eliminating any possibility of operating failure as a result of disengagement of these elements.

Still another object of the invention is to provide an evacuator of the above type, which may readily be strapped to the body of a patient so that drainage may take place without interfering with the patient's freedom of movement.

Briefly stated, these objects are accomplished in a surgical evacuator constituted by a cup of transparent, rigid plastic material covered by an elastic membrane to define a fluid-tight sump chamber. The rigid side wall of the cup is provided with an inlet fixture to which is coupled a drain tube leading to the surgical site, and an exhaust fixture which accommodates a removable plug or other means to open and close the exhaust.

Attached to the membrane is a rigid disc functioning as a piston or actuator, such that when the plug is removed and the disc depressed, the membrane is stretched inwardly to reduce the volume of the sump chamber, thereby displacing the atmosphere, which is discharged through the open exhaust. Thereafter, when the exhaust is closed and the disc released, the stretched membrane proceeds to recover its original form, thereby creating a negative pressure acting to draw fluid from the surgical site through the tube and into the sump chamber.

OUTLINE OF THE DRAWING

For a better understanding of the invention, as well as other objects and further features thereof, reference is made to the following detailed description to be read in conjunction with the accompanying drawing, wherein:

FIG. 1 is a perspective view of a manually-operated evacuator in accordance with the invention;

FIG. 2 is a section taken through the evacuator in its static state;

FIG. 3 is a section showing the evacuator when the cover membrane thereof is stretched to create a suction force; and FIG. 4 shows the evacuator strapped onto a patient.

DESCRIPTION OF THE INVENTION

Referring now to the drawing, and more particularly to FIGS. 1 and 2, a surgical evacuator in accordance with the invention, generally designated by numeral 10, includes a cup fabricated of rigid, transparent plastic material of good mechanical strength, such as polypropylene. The cup comprises a cylindrical side wall 11, a flat bottom 12, and a peripheral flange 13 encircling the lip of the cup.

The cup is covered by an elastic membrane 14 which is capable of being stretched to an extent sufficient to displace the atmosphere from the cup. Membrane 14 may be made of a rubber, neoprene, or a thin injection-molded thermoplastic elastomeric sheet having a circular profile. The margin of the membrane is secured to the mouth of the cup by means of a metal ring 15 having a collar portion 15A which telescopes within cylindrical side wall 11, and an annular portion 15B which lies against flange 13. The margin of membrane 14 is sandwiched between ring 15 and the cup, and is bonded thereby by a suitable epoxy or other adhesive effecting an hermetic seal, thereby defining a fluid-tight sump chamber 16 within the cup.

Mounted on side wall 11 is an inlet fixture 17 communicating with sump chamber 16, and having a pipe extension adapted to be coupled to the end of a drain tube 18 leading to the surgical site. In practice, the input end of tube 18 is inserted in the wound at a point where evacuation is desired, the wound then being closed by suturing, in the usual manner. Where several points are to be evacuated, drain pipe 18 may be linked to these points by a manifold coupled to the branch tubes.

The drain tube or tubes are constructed of flexible plastic or other material which is non-reactive to the body constituents and are of sufficient rigidity to prevent the wall of the tube from collapsing when negative pressure is created by the evacuator. The internal diameter of the tube must be sufficient to accommodate the fluids being drained.

Also mounted on side wall 11 is an exhaust fixture 19 communicating with sump chamber 16 and associated with a removable stopper plug 20 making it possible to open and shut the exhaust. The plug is attached on the free end to a flexible strap 21 anchored in the exhaust fixture to prevent the loss thereof. Alternatively, the exhaust fixture may incorporate a simple valve capable of opening and closing the exhaust.

Attached centrally to the upper face of membrane 14 is a disc 22 which may be made of plastic or other rigid material. Disc 22 is preferably joined to membrane 14 only at its center to permit the portion of the membrane lying thereunder to stretch. This is accomplished by applying a bonding agent to the membrane through a central bore in the disc, which forms a locking head 23.

In practice, after drain tube 18 is installed, stopper plug 20 is temporarily removed from the exhaust fixture and pressure is manually applied to actuator disc 22, as shown in FIG. 2, to stretch membrane 14 inwardly, thereby forcing the atmosphere out of sump chamber 16 through the open exhaust fixture 19. While the membrane is so stretched, plug 20 is reinserted in the exhaust fixture to shut the exhaust and thereby seal the pump chamber. The actuator disc is then released to create a negative pressure in the sump chamber as the membrane moves upwardly and proceeds to recover its original form.

The resultant vacuum causes fluids from the body to be drawn into the sump chamber. This continues until the sump chamber has been filled to a point where the action of the membrane is exhausted. At this point, the stopper plug may be removed and the fluid in the sump chamber drained therefrom through the exhaust, after which the drainage cycle, as described above, may be repeated. Since the cup is transparent, one can readily see whether the evacuator is functioning properly.

It is desirable in some instances to strap the evacuator onto the patient so that he is not confined to his bed and is free to move about. With such ambulatory patients, the evacuator is attached to the body of the patient by suitable straps 24 and 25, as shown in FIG. 4, which are connected to flange 13 through holes 13a, 13b, 13c and 13d, bored therein.

An evacuator structure of the type disclosed herein is of exceptionally simple construction and operates very efficiently. Because it is inexpensive to manufacture, one can afford to discard the evacuator after a single use, so that each patient is supplied with a new, sterile unit, thereby obviating the need to clean and resterilize the unit. Preferably, the unit and its associated drain tubing and straps are packaged as a complete kit in a sterile package.

In order to ensure an hermetic seal of the chamber, it may be desirable to combine membrane 14 with a thin film of impermeable material such as polyurethane, the film serving to prevent air leaks. A rubber membrane may incorporate minute pores, but when combined with a sealant film, leakage is avoided. Also, instead of adhering disc 22 to the membrane, one may mechanically lock the disc thereto by the use of a small rubber ball which is interposed between the membrane and the sealant film, and is forced through a central opening in the disc to provide a connecting knob.

While there has been shown and described a preferred embodiment of surgical evacuator in accordance with the invention, it will be appreciated that many changes and modifications may be made therein without, however, departing from the essential spirit of the invention. For example, to facilitate operation of the evacuator, one may provide a pump lever which is pivoted on the flange 13 and is provided with a hammer head adapted to engage disc 22. In this way, relatively little manual pressure is required to depress the membrane.

Also, while the surgical evacuator has been shown with a separate inlet fixture 17 and an exhaust fixture 19, a single fixture may be provided serving both as an inlet and an exhaust. In this single-fixture arrangement, the procedure is to first depress actuator disc 22 to force the atmosphere out of sump chamber 16 through the open fixture 17 (fixture 19 is omitted). Then drain pipe 18, whose input end is inserted in the wound at a point where evacuation is desired, is coupled to fixture 17, and disc 22 is released to produce a suction force acting to draw fluids from the body into sump chamber 16.

We claim:

1. A self-contained, independently-operatable surgical evacuator unit adapted to drain fluid from a body site and to transfer the fluid to the unit, said unit comprising:
    (A) a cup formed of rigid transparent plastic material and having a continuous side wall and an unbroken bottom wall,
    (B) an elastic membrane formed of rubber covering the cup and sealed to the lip thereof to define a sump chamber to hold fluid, said membrane in its unstretched state being substantially planar,
    (C) an inlet-exhaust fixture mounted on said side wall and communicating with said chamber, said fixture when functioning in an inlet mode being adapted for connection to a drain tube leading to a body site to be drained, said fixture when functioning in an exhaust mode being disconnected from said drain tube, and
    (D) an actuator disc secured to said membrane and manually-operable by an inwardly-directed force to effect inward stretching of said membrane to displace the atmosphere of said chamber through said fixture in the exhaust mode in which it is disconnected from the drain tube and to create in the inlet mode of said fixture in which it is connected to the drain tube a negative pressure acting to draw fluid into said chamber when the disc is released, said membrane then being capable of returning to its original unstretched state without the use of an external force whereby fluid withdrawn from the body site proceeds to fill said chamber.

* * * * *